United States Patent [19]

Isselbacher et al.

[11] 4,261,976

[45] Apr. 14, 1981

[54] METHOD AND GLYCOPROTEIN COMPOSITION FOR INHIBITION OF GROWTH OF TRANSFORMED CELLS AND TUMORS

[75] Inventors: Kurt J. Isselbacher, Newton Centre; Daniel K. Podolsky, Boston, both of Mass.; Milton M. Weiser, Buffalo, N.Y.

[73] Assignee: The Massachusetts General Hospital, Boston, Mass.

[21] Appl. No.: 948,252

[22] Filed: Oct. 3, 1978

[51] Int. Cl.$^3$ .................... A61K 35/12; A61K 35/16; A61K 37/02; C07G 7/00
[52] U.S. Cl. ................................ 424/95; 260/112 B; 260/112 R; 424/101; 424/177; 435/177; 435/193
[58] Field of Search ...................... 260/112 R, 112 B; 424/101, 95, 112 B, 177

[56] References Cited

U.S. PATENT DOCUMENTS

| | | |
|---|---|---|
| 3,607,650 | 9/1971 | Maslianico et al. ......... 260/112 R X |
| 3,823,126 | 7/1974 | Bjorklund ....................... 260/112 R |
| 3,928,580 | 12/1975 | Fontaine ..................... 260/112 R X |
| 4,042,576 | 8/1977 | Eustache .......................... 260/112 R |

OTHER PUBLICATIONS

Int. Arch. Allergy, vol. 36, pp. 191-203 (1969), Bjorklund.

Primary Examiner—Howard E. Schain
Attorney, Agent, or Firm—Paul J. Cook

[57] ABSTRACT

A glycoprotein which inhibits the growth of malignant cells or malignant tumors is obtained from animals and humans having malignant cells or tumors. The glycoprotein has a molecular weight of about 3600 and is a substrate for both the GT-I and GT-II isoenzymes of serum galactosyltransferase. The glycoprotein is isolated by subjecting a body fluid or extract of the malignant cells or tumors containing the protein to serial column separation steps with materials which concentrate glycoprotein and separate a fraction having a molecular weight of about 3600. The effective form of the glycoprotein as set forth herein is intended to include the glycoprotein as well as its physiologically and pharmacologically active metabolites in the body.

8 Claims, 10 Drawing Figures

METHOD AND GLYCOPROTEIN COMPOSITION FOR INHIBITION OF GROWTH OF TRANSFORMED CELLS AND TUMORS

BACKGROUND OF THE INVENTION

This invention relates to a method and composition for inhibiting the growth of cancerous cells and tumors.

The enzymes known generically as glycosyltransferases participate in the biosynthesis of complex carbohydrates. They are commonly found as membrane-bound enzymes within the interior of the cell. The function of adding sugars to proteins is not clear, although the nature of the terminal sugar appears to be important in the control of secretion and in the clearance of circulating glycoproteins and the biosynthesis of ABO blood group substances also requires sugar additions through the action of glycosyltransferases. Although some glycosyltransferases appear to be membrane-associated enzymes when prepared from tissue homogenates, these transferases have also been detected as soluble enzymes in various body fluids, including rat and human serum.

It has been reported in Biochemical and Biophysical Research Communications, Vol. 65, No. 2, pp. 545-551 and proceedings of the National Academy of Sciences, U.S.A., Vol. 73, No. 4, pp. 1319-1322 that there exists two isoenzymes of serum galactosyltransferase. The isoenzyme identified as GT-II was shown to be found predominantly in patients with neoplastic disease. There is a correlation of serum GT-II levels with the extent of malignancy which apparently is independent of the site of the neoplasm. The preoperative level of GT-II activity appears to correlate with the overall extent of the tumor. Thus, the level of serum GT-II increases in association with the progression of the disease. It is not known whether the galactosyltransferase (GT-II) is merely produced by the cancerous cells or is somehow involved in the mechanism of cancerous cell reproduction.

SUMMARY OF THE INVENTION

The present invention is based upon the discovery that a substrate for the galacosyltransferase isoenzyme (GT-II) also has the characteristic of inhibiting growth or destroying cancerous cells and/or cancerous tumors. The inhibitor is found present in the cancerous cells or malignant tumors or in the body fluids such as sera of animals, including humans which are afflicted with cancer. The inhibitor also is found in vitro in transformed animal cells. The inhibitor is obtained by subjecting either the body fluid containing the inhibitor or the fluid obtained from malignant cells to a separation procedure which includes a step for concentrating glycoproteins from the fluid being treated and at least one chromatographic step in order to recover a fraction of glycoprotein having a molecular weight of about 3600, ±3000. When this inhibitor is administered to animals having a cancerous tumor or to malignant cells in vitro, growth of the malignant tumor or cells is inhibited and/or the tumor or cells are selectively destroyed without significant destruction of normal cells.

DESCRIPTION OF SPECIFIC EMBODIMENTS

The present invention is based upon the surprising discovery that malignant cells and/or malignant tumors produce a substrate or acceptor for the galactosyltransferase isoenzymes, GT-I and GT-II, particularly in advanced stages of malignancy. The second surprising discovery is that the inhibitor, when concentrated above the natural concentrations produced by the tumors or cells has the effect of inhibiting malignant cell or malignant tumor growth and, in some cases, has the effect of selectively destroying malignant cells and malignant tumors without significant destruction of normal cells. This latter effect is surprising because the inhibitor, in the concentration produced naturally within the body of animals does not have the effect of inhibiting malignant cell or tumor growth even though it is present in the body of the animal in higher concentrations as the malignancy becomes more advanced within the body. This same effect is observed with malignant cells grown in vitro.

The presence of the inhibitor acceptor was initially detected by the inhibition of the incorporation of radiolabeled galactose into an acid-precipitable reaction product of galactose, galactosyltransferase and SGF-fetuin (fetuin minus terminal sialic acid and penultimate galactose). Serum and effusions from patients with metastatic disease contained a substance which inhibited incorporation into the acid-precipitable SGF-fetuin acceptor. This inhibition of activity was not found in sera from patients with localized disease, normal or disease controls. Inhibition of galactosyltransferase/SGF-fetuin acceptor activity was found to be linearly related to the amount of inhibiting serum added. That the inhibition of the observed incorporation into an acid-precipitable product was due to the presence of a competitive substrate was determined by the finding that sera and effusion which contained the inhibitor activity demonstrated competitive inhibition for SGF-fetuin but not for UDP-galactose; the latter reaction being disclosed generally by Lineweaver et al (1934), J. Amer. Chem. Soc., 56, 658-666.

The purified inhibitor of this invention is obtained from animal body fluids containing the inhibitor such as serum or from malignant cells or malignant tumors either in vivo or in vitro. The liquid containing the inhibitor is subjected to at least two serial separations in a column. In one column, the separating material comprises a composition which functions to isolate glycoprotein from the remaining components in the fluid being separated. The second column contains a separating material which functions chromatographically to separate the materials in the body fluid being treated, generally on the basis of molecular weight in order to isolate a fraction having a molecular weight of about 3600, +3000. In the process of this invention, the sequence of glycoprotein separation and chromatographic separation is not critical; that is, the glycoprotein separation can precede the chromatographic separation or vice versa. While the product of this invention can be purified substantially 100% by multiple chromatographic steps, it has been found that only one chromatographic step is sufficient in order to obtain a product which has the property of inhibiting the growth of malignant cells or malignant tumors. Thus, the product of this invention can contain components of the body fluid or cell extract which do not adversely affect the substrate property of inhibiting the growth of malignant cells or tumors.

Representative suitable materials which function to separate glycoproteins from other constituents in body fluids include charcoal/celite, Sephadex, Sepharose, ion exchange resins, or the like. Representative suitable materials which function to separate body fluids, generally on the basis of molecular weight in order to obtain a fraction having a molecular weight of about 3600± about 3000, include DEAE cellulose, Sephadex, Sepharose or the like.

In a preferred embodiment of the process of this invention, the glycoprotein isolating step precedes the chromatographic step in order to rapidly achieve a large degree of purification. Furthermore, it is preferred that the body fluid containing the inhibitor be subjected to a preliminary separation step by filtration through a microfilter having generally uniform pores, such as those obtained from Amicon Corporation or Millipore Corporation, in order to remove high molecular weight components of the body fluid such as those having a molecular weight of above about 5,000, preferably above about 10,000. In addition, it is preferred to utilize an evaporation step between columnar separations in order to further concentrate the inhibitor prior to the last column separation step. The inhibitor of this invention is concentrated in the glycoprotein fraction having a molecular weight of about 3600±3000 which generally is the first fraction obtained from the chromatographic separation step.

The inhibitor of the present invention is a glycoprotein. Carbohydrate analysis shows that the carbohydrate portion of the molecule comprises primarily glucosamine and mannose. The peptide portion of the molecule when analyzed by gas liquid chromatography shows eight amino acids comprising alanine, glycine, leucine, serine, asparagine/aspartic acid, glutamine/glutamic acid, lysine and tyrosine.

The purified inhibitor of this invention exhibits a profound effect for the inhibition of growth or for the selective destruction of transformed cells and tumors. This effect is unexpected since the inhibitor, in its natural state, appears to increase in concentration with an increase in the stage of malignancy of cells or tumors in the body of an animal. Accordingly, the property of inhibition of transformed cell and tumor growth appears to contradict observations of the inhibitor in its natural environment. The glycoprotein inhibitor of this invention is administered to an animal including a human intraperitoneally, subcutaneously, orally or intravenously. Generally, the dosage of administration is between about 1 and about 1000 micrograms per kilogram of animal, more usually between about 5 and about 50 micrograms per kilogram of animal. Inhibition of cell and tumor growth has been observed for both lower animal malignant cells and for human malignant cells in nitro and for lower animal cells in vivo.

The following examples illustrate the present invention and are not intended to limit the same.

EXAMPLE I

This example illustrates the process for obtaining the glycoprotein inhibitor of this invention and characterizes the inhibitor.

UDP-[1-$^3$H] galactose (2.25 Ci/mmol) was obtained from New England Nuclear (Boston, Mass. USA). A stock solution (714 μM) was prepared to a final specific radioactivity of 0.288 Ci/mmol by using unlabelled UDF-galactose obtained from Sigma Chemical Co. (St. Louis, Mo. USA). Fetuin lacking terminal sialic acid and penultimate galactose residues (SGF-fetuin) was prepared as previously described by Kin et al., J. Biol. Chem., 246, 5466-5476.

PREPARATION OF INHIBITOR

Sera were obtained from human patients having various malignancies. Sera Samples were prepared by centrifugation at 100 G for 10 min. at 4° C. and stored at 4° C. before use. Samples containing the acceptor/inhibitor were heat-inactivated (20 min., 45° C.) and precipitate was removed by centrifugation at 2000 G for 5 min. at 4° C. to eliminate enzyme activity.

PREPARATION OF GALACTOSYLTRANSFERASE ENZYME SOURCES

Pooled malignant effusion containing both isoenzyme GT-I and GT-II activities, as determined by previously described techniques (Podolsky Weiser, 1975, Biochem. Biophys. Res. Commun., 65, 545-551), was used as enzyme source after partial purification by (NH$_4$)$_2$SO$_4$ precipitation in which the galactosyltransferase isoenzymes are separated from proteins with different solubility in (NH$_4$)SO$_4$ solutions. Enzyme from the 30-70%-(w/v)—(NH$_4$)$_2$SO$_4$ factor was suspended in 0.1 M-sodium cacodylate, pH 7.4, and dialysed against this buffer to give a final activity of 2000 cpm/h/10 μl with SGF-fetuin as acceptor as described below. Purified isoenzymes GT-I and GT-II were prepared from human malignant effusion by sequential chromatography on columns containing DEAE-cellulose, α-lactalbumin-Sepharose and N-acetylglucosamine-Sepharose.

ASSAY OF GALACTOSYLTRANSFERASE ACCEPTOR ACTIVITY

Galactosyltransferase activity was measured by modification of previously described methods (Podolsky & Weisner, Biochem. J., 146, 213-221 and Biochem. Biophys. Res. Commun., 65, 545-551). In one assay, acceptor activity was detected by the ability of acceptor samples to inhibit competitive incorporation of labelled galactose into the acid-precipitable acceptor. Assay mixture included 10 μl of enzyme source, 7.5 μl of UDP-[1-$^3$H] galactose stock solution, 35 μl of 0.1 M-sodium cacodylate, pH 7.4, and 0.154 M-NaCl, 7.5 μl 0.1 M-MnCl$_2$ and SGF-fetuin (0.2 μM-acceptor sites) in a volume of 20 μl, with 10 μl of sample being added to test for inhibition. The mixture (85 μl) was incubated for 60 min at 37° C. The reaction was then terminated by addition of 5% (w/v) phosphotungstic acid in 2 M—HCl and incorporation of radioactive label into acid-precipitable material was determined as previously described by Podolsky & Weisner, Biochem., J., 146, 213-221. Inhibition was calculated as the difference of incorporation between assay mixture with and without addition of sample.

Direct measurement of acceptor activity was done by using an assay mixture identical with that described above except that 20 μl of the sample being tested replaced SGF-fetuin. At the end of the incubation, the reaction mixture was applied to Whatman 3 MM paper, which was then electrophoresed in 1% (w/v) sodium tetraborate buffer, pH 8.0, at 1000 V for 50 min. Strips were evaluated either by a Packard radiochromatogram scanner or, after cutting into 2 cm wide pieces, by counting in a Beckman scintillation counter in a toluene-based scintillation fluid (Podolsky & Weiser, Biochem. J., 146, 213-221, 1975). The acceptor remained near the origin, whereas UDP-[1-$^3$H] galactose and its breakdown products moved toward the anode.

IDENTIFICATION OF PRODUCT

To determine the identity of incorporated radioactivity, reaction mixtures were scaled up tenfold and reaction time was increased to 90 min. After termination of the reaction and electrophoresis as above, product was eluted and then hydrolysed in 1.0 ml of 2 M-HCl at 100° C. for 6 hours. The hydrolysate was subjected to ion-exchange chromatography through a column (1.5 cm × 10 cm) containing AG 1/×8 (formate form, 200–400 mesh) ion-exchange resin. The eluates were concentrated to 100 µl under nitrogen and 40 µl samples applied to Whatman 1 MM paper. Descending chromatography was subsequently performed as previously described by Podolsky & Weiser, Biochem. J., 146, 213–221 and migration of label was compared to genuine sugar standards.

PURIFICATION OF CANCER-ASSOCIATED GALACTOSYLTRANSFERASE ACCEPTOR

Pooled human malignant effusion (1.4 liters) previously found to contain acceptor activity was heat-inactivated (65° C., 45 min) and precipitate removed by centrifugation (5000 g × 30 min). The supernatant was then passed through a filtration membrane with an exclusion size of 10,000 mol. wt. (PM-10 membrane, Amicon Co., Lexington, Ma, USA) and the ultrafiltrate obtained. Total hexose (Dubois et al, Biol. Chem., 28, 350–356, 1956) and protein (Lowry et al, J. Biol. Chem., 193, 1672–1676, 1951) were determined and an activated charcoal/Celite column (1:1, w/w) was prepared by using 1 g of gel to 1 mg of hexose per sample. The total sample was applied and the column washed with 10 ml of water/ml of gel. Sequential elution with increasing concentrations (v/v) of ethanol (17%, 20%, 25%, 30%, 50%) was performed with different amounts of eluent for each concentration (25,20,10,10,25 ml/ml of gel, respectively). The fractions were assayed for hexose, protein and acceptro activity as above.

Subsequently, the charcoal/Celite fraction containing the acceptor was concentrated by evaporation under vacuum to 2.5 ml and then applied to a column of DEAE-cellulose (0.9 cm × 65 cm) equilibrated in 0.0005 M-sodium phosphate buffer, pH 7.6. After washing with the application buffer (100 ml), the column was developed with a linear ascending gradient of 0.0005–0.03 M-sodium phosphate buffer, pH 7.6, at a rate of 20 ml/h; 5.0 ml fractions were collected. Protein (evaluated by continuous $A_{280}$ monitoring) and hexose were determined for each fraction. Peaks of protein and hexose were individually pooled and acceptor activity was determined. The peak acceptor activity was evaluated for homogeneity by using Whatman 1 MM paper in three paper-electrophoretic solvent systems (A, pyridine/acetic acid, pH 3.0, 500 V for 3.5 hrs; C, 0.05 M—$Na_2HPO_4$, pH 8.5, 300 V for 5 hrs) and a descending paper-chromatography system ethyl acetate/pyridine/water/acetone, 10:5:10, by vol. (Johansen et al, Biochem., 1961). Molecular weight was estimated by chromatography on a column (2.5 × 100 cm) of polyacrylamide gel (BioGel P-10; BioRad Laboratories, Los Angeles, CA., USA) developed with distilled water at a rate of 16 ml/h, 5.0 ml fractions were collected. Standards included vitamin $B_{12}$, ribonuclease, $\beta$-lactalbumin and Blue Dextran (Sigma Chemical).

CARBOHYDRATE AND AMINO ACID COMPOSITION

Measurement of sugar composition was made by assaying the purified endogenous acceptor after acid hydrolysis (6 M—HCl, 90° C., 120 min). Hexose was determined by the phenol—$H_2SO_4$ method (Dubois et al, Anal. Chem., 28, 350–356, 1956) and hexosamine by the Elson-Morgan assay (Blix, Acta. Cehm. Scand., 2, 467–473, 1948). Qualitative evaluation of the sugar composition was obtained by application of the hydrolysate to two descending chromatography systems as described by Podolsky & Weiser, Biochem. J., 146, 213–221, 1975. Sialic acid composition was determined after hydrolysis of the intact acceptor with 0.05 M $H_2SO_4$ at 80° C. for 60 min by using the thiobarbituric assay of Warren, J. Biol. Chem., 234, 1971–1975,1959. Inositol (25 µg) was added as an internal standard to purified acceptor (125 µg) before drying. The dried material was incubated in 1.0 ml of methanolic 1 M—HCl at 85° C. for 60 min, then evaporated again to dryness under $N_2$ and washed with methanol. A stock solution (0.1 ml) of Syland HRP (Supelco Co., Madison, Wisc., USA) was added and the suspension left at room temperature for 60 min. After drying, material was extracted with 60 l of hexane and 1 µl of this extract applied to a column (152 cm × 0.3 cm) of OV17 (0.1%, g.l.c. 110 support; mesh 120–140; Supelco Co.) by using a Perkin-Elmer 900 g.l.c. instrument programmed over 75°–250° C. at a rate of 10° C./min.

Amio acid analysis was carried out by modification of the method of Zumwalt et al, J. Chromatogr., 52, 171–194, 1970. After derivative formation with trifluoroacetic anhydride in dichloromethane, 1.5 µl was applied to columns of polyethylene glycol adipate of OV-225 by conditions described earlier by Podolsky & Weiser, Biochem. J., 146, 213–221, 1975.

Figure 2:
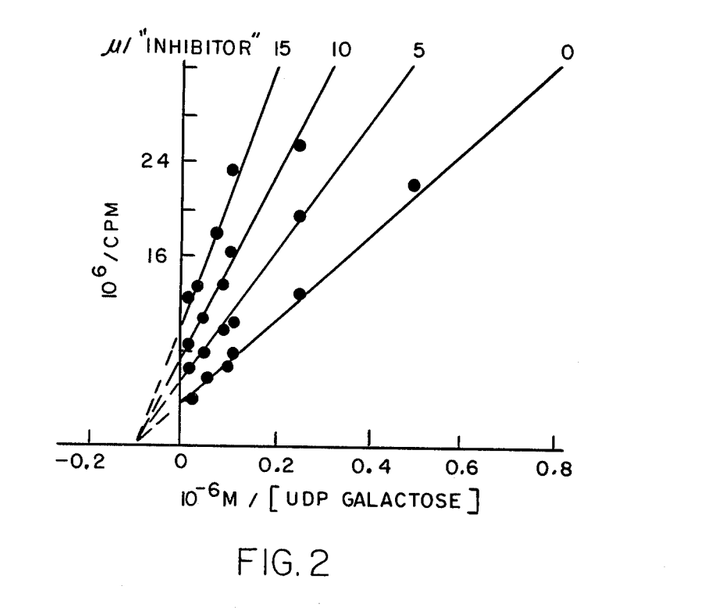
Figure 3:
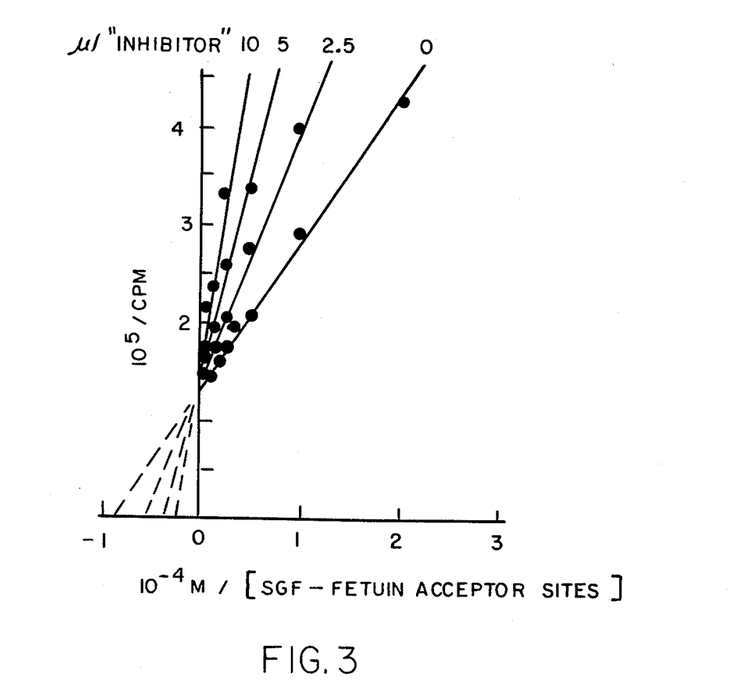

The presence of an acceptor was initially detected by the inhibition of UDP-galactose-SGF-fetuin galactosyltransferase activity. As FIG. 1 reveals, serum and effusions from patients with metastatic disease contained a substance which inhibited incorporation into the acid-precipitable SGF-fetuin acceptor. This inhibition of activity was not found in sera from patients with localized disease, normal or disease controls. Inhibition of galactosyltransferase/SGF-fetuin acceptor activity was found to be linearly related to the amount of inhibiting serum added. That the inhibition of the observed incorporation into an acid-precipitable product was due to the presence of a competitive substrate was suggested by the finding that sera and effusion which contained the inhibitor activity demonstrated competitive inhibition for SGF-fetuin, but not for UDP-galactose as determined by Lineweaver-Burk, J. Amer. Chem. Soc., 56, 658–666, 1934 plots (FIGS. 2 and 3).

Figure 4:
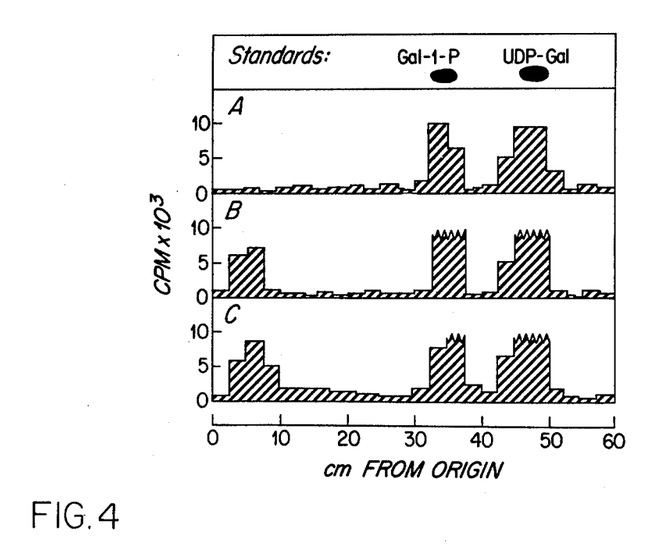
Figure 5:
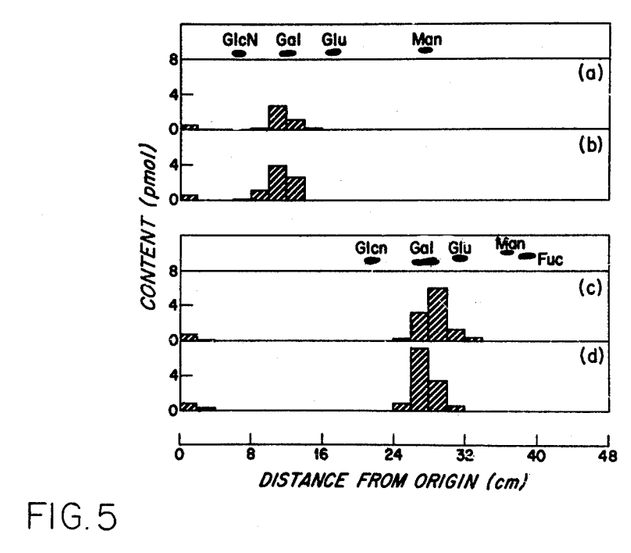

The presence of galactosyltransferase acceptor in sera and effusions was confirmed by observation of direct incorporation of galactose into a product which was separated by paper electrophoresis. FIG. 4 shows the appearance of a peak radioactive incorporation near the origin which was absent from controls or samples lacking capacity to inhibit incorporation into SGF-fetuin. This peak was eluted, and the identity of the incorporated labelled compound demonstrated to be galactose in two descending chromatography systems after acid hydrolysis of the reaction produce (FIG. 5).

The acceptor activity was found to be diffusible in convention dialysis tubing. Purification was begun by removing high-molecular-weight material (mol. wt.>10,000) from heat-inactivated human malignant effusion. The ultrafiltrate from an Amicon PM-10 micropore membrane was applied to a charcoal/Celite column and the column developed with increasing concentrations of ethanol in a stepwise fashion. As Table 1 demonstrates, the inhibitor to galactosyltransferase:SGF-fetuin acceptor activity was found in the first fraction. No comparable inhibition could be detected in the elution of columns on which controls (non-malignant effusions and malignant effusion with no detectable inhibition activity) were chromatographed.

Analysis of the inhibiting fraction (C1) (Table 1) showed that it had protein as well as significant amounts of hexose, with no detectable phosphate, lipid or nucleic acid; this suggested that the inhibitor/acceptor purity material in fraction C1 was chromatographed on a column of DEAE-cellulose, by using a gradient of increasing concentration of phosphate buffer. As FIG. 6 demonstrates, three peaks of material which contained both carbohydrate (neutral hexose by the phenol/$H_2SO_4$ method) and protein were detected on elution of this column. All inhibitor/acceptor activity was contained within the first peak (fractions 8-12) (Table 2). This material was pooled and found to be homogeneous in three paper-electrophoretic solvent systems and a descending paper-chromatographic system set forth above. In each system, material stained for carbohydrate and protein co-chromatographed.

After acid hydrolysis, the purified acceptor was analysed for carbohydrate content by chemical assay and by g.l.c. As Table 3 shows, the purified acceptor contains hexose and hexosamine as well as some sialic acid by chemical analysis. Qualitative descending chromatography of the acid hydrolysate revealed the presence of mannose and glucosamine. These results were confirmed by g.l.c. (Table 3).

Amino analysis by g.l.c. revealed the presence of eight acids (Table 4). The most notable feature of the amino acid composition is the presence of two residues of asparagine and one residue of serine and no detectable threonine. An approximate mol. wt. of 3600 was determined by polyacrylamide-gel chromatograph.

The acceptor activity of the purified glycopeptide was measured directly after incubation by separating the glycopeptide by paper electrophoresis as described above. Labelled product was found to co-migrate with purified acceptor (FIG. 4c), and also to co-chromatography with the purified acceptor in a descending chromatography system. The labelled acceptor was eluted from the chromatograms and the radioactive label identified after acid hydrolysis. All label was found to co-migrate with galactose in two solvent systems (FIG. 5b), confirming the identity of the substance as a cancer-associated galactosyltransferase acceptor.

Finally, the activity of the purified acceptor was assayed by using purified galactosyltransferase isoenzymes (GT-I and GT-II) as enzyme sources. As FIG. 7 demonstrates, the acceptor could be used as a substrate by both normal and cancer-associated isoenzymes. However, determination of Michaelis constant, by assuming a mol. wt. of 3600, indicated that the cancer-associated isoenzyme had a significantly higher affinity ($K_m = 20$ μM) for the acceptor than the normal isoenzyme ($K_m = 500$ μM).

Figure 1:
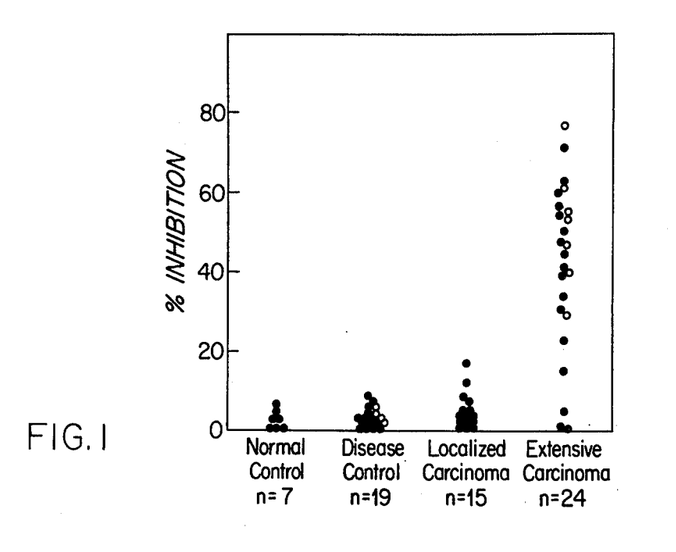

As FIG. 1 demonstrates, there was significant inhibition of galactosyltransferase activity by sera and effusions obtained from patients with extensive metastatic cancer. This inhibition was subsequently shown not to be competitive with UDP-galactose (FIG. 2), but rather caused effective competitive inhibition of the exogenous acceptor SGF-fetuin used in the galactosyltransferase activity by several effusions was then correlated with the presence in these fluids of a galactosyltransferase acceptor substrate which could be detected after separation by paper electrophoresis (FIG. 4). The inhibitor/acceptor was purified (FIG. 5, Tables 1 and 2) and found to be a glycopeptide of approx. 3600 mol. wt. with a composition of almost 70% carbohydrate (Table 2). The purified glycopeptide was shown to be a galactose acceptor for galactosyltransferase activity (FIGS. 4 and 5), and because of its occurence in fluids from patients with metastatic cancer, it is referred to as a cancer-associated galactosyltransferase acceptor.

Since this acceptor is a glycopeptide, one would have expected that its presence in fluids would have added to the total galactosyltransferase activity. Its detection as an inhibitor may be explained by the method of assay. The product of galactosyltransferase activity utilizing SGF-fetuin as acceptor is detected as an acid precipitate. Glycopeptides of relatively low molecular weight (<10,000) are not effectively precipitated by acid, especially if they have a high carbohydrate and low peptide content. In subsequent experiments the purified glycopeptide was found to remain soluble in the phosphotungstic acid/HCl mixture.

The cancer-associated galactosyltransferase acceptor is notable for its limited content of carbohydrates and amino acids. Carbohydrate analysis by g.l.c. or by qualitative descending chromatography after acid hydrolysis demonstrated only glucosamine and mannose in significant quantities (Table 3). The peptide portion when analysed by g.l.c. was composed of only eight different amino acids (Table 4). The cytotoxic polypeptide purified from tumor fluids by Sylvén & Holmberg, European Journal of Cancer Vol. 1, pp 199-202, 1968, also consisted of only a few amino acids, which were similar to those described here. However, that substance was apparently devoid of carbohydrate (Sylvén & Holmberg, 1968).

FIG. 1 shows inhibition of galactosyltransferase: SGF-fetuin activity by human sera and effusions. Pooled 30-70%(w/v)—$(NH_4)_2SO_4$ fraction of human malignant effusion was used as enzyme source. Galactosyltransferase activity was assayed by using SGF-fetuin acceptor with or without the heat-inactivated sample (10 μl) being tested for inhibitor activity as described above and inhibition calculated as the difference between activity in presence and absence of heat-inactivated sample. Normal controls were 12 healthy laboratory personnel. Disease controls included seven patients with pancreatitis (two acute, five chronic), four patients with cholecystitis and four patients with peptic ulcer disease. Effusions were from patients with cirrhosis (three) or congestive heart failure (two). Patients with localized carcinoma had either carcinoma of colon and rectum (12) without evidence of lymphatic invasion at surgery, or breast carcinoma (three) without evidence of spread at subsequent surgery. Patients with extensive carcinoma (15 colon, six breast, four lung, four pancreas) had evidence of massive hepatic or bone metastases or malignant effusion. Sera (0), effusions (0).

FIG. 2 shows the effect of increasing amounts of the inhibitor on $K_m$ for UDP-galactose of UDP-galactose, fetuin galactosyltransferase activity. Determinations of $K_m$ for UDP-galactose were performed by using a complete reaction mixture which included 10 μl of enzyme diluted with 55 μl of 0.1 M-sodium cacodylate, pH 7.4, 10 l of SGF-fetuin containing 0.2 μM-acceptor sites and 35 μl of UDP-1-$^3$H galactose in increasing concentrations. Samples were incubated at 37° C. for 120 min, reaction was stopped and activity determined as cpm/mg of protein as described above. Data are plotted by the Lineweaver-Burk (1934) method. Determinations were made in the presence or absence of increasing amounts of human heat-inactivated inhibitor prepared from pooled sera as described above.

FIG. 3 shows the effect of increasing amounts of inhibitor on the $K_m$ for SGF-fetuin of UDP-galactose-SGF-fetuin galactosyltransferase activity. $K_m$ for SGF-fetuin was determined with a reaction mixture which included 10 μl; of enzyme, 55 μl of 0.2 M sodium cacodylate, pH 7.4, 10 μl of 0.15 M-MnCl$_2$, 15 μl of UDP [1-$^3$H] galactose stock prepared as described above and increasing amounts of SGF-fetuin in 60 μl. Assay conditions were as described above in FIG. 2. Data are plotted by the Lineweaver-Burk (1934) method in the presence or absence of increasing amounts of human heat-inactivated inhibitor prepared pooled sera as described above.

FIG. 4 is a demonstration of galactosyltransferase acceptor activity of malignant serum and purified glycopeptide. Galactosyltransferase activity was assayed as described above by using either heat-inactivated pooled serum or 3 μg of purified glycopeptide instead of SGF-fetuin as acceptor. Enzyme source was the partially purified preparation from pooled effusions. After incubation, mixtures were evaporated to dryness, then resuspended in 15 μl of water for application to Whatman 3 MM paper. Paper electrophoresis was performed in a 1% (w/v) sodium tetraborate buffer, pH 8.8, at 1000 V for 50 min. After electrophoresis, strips were cut into 2 cm-wide pieces and radioactivity was determined by counting in toluene-based scintillation fluid. Mobility is compared with UDP-galactose (UDP-Gal) and galactose 1-phosphate (Gal-1-P) standards.

(a) Control, no acceptor added. (b) Representative chromatogram with inhibitor-containing serum (see FIG. 1). (c) Purified inhibitor (from peak I, FIG. 6). Chromatograms of sera from normal controls, disease controls and patients with localized carcinoma were similar to (a).

FIG. 5 illustrates product identification of UDP-galactose-cancer-associated glycopeptide acceptor galactosyltransferase activity. Assays were performed as described above and in FIG. 4, except that reaction mixtures were concentrated and applied to Whatman 3 MM paper for electrophoresis as described in FIG. 4. The radioactivity incorporated into the new peak located near the origin (FIGS. 4b and 4c) was eluted and concentrated to near dryness under nitrogen. After acid hydrolysis (2 M HCl, 100° C., 6 h), the hydrolysate was subjected to ion-exchange chromatography through a column (1.5 cm×19 cm) containing AG 1-X8 (formate form; 200-400 mesh) ion-exchange resin. Eluates were concentrated to 100 μl samples and applied to Whatman 1 MM paper. Chromatography was performed in two solvent systems: (a,b), butanol/ethanol/water 10:1:2, by vol.), 110 h; (c) (d), ethyl acetate/pyridine/water (12:5:6 by vol.), 15 h. Chromatograms were then cut into 2 cm strips and radioactivity was determined by counting in a Beckman scintillator counter, in a toluene-based scintillation fluid. Migration of genuine carbohydrate standards was determined by AgNO$_3$ stain (a), (c), Crude effusion as a source of acceptor, (b), (d) purified glycopeptide (from FIG. 6, peak 1) as acceptor source. GlcN, glucosamine; Gal, galactose; Glu, glucose; Man, mannose; Fuc, fucose.

Figure 6:
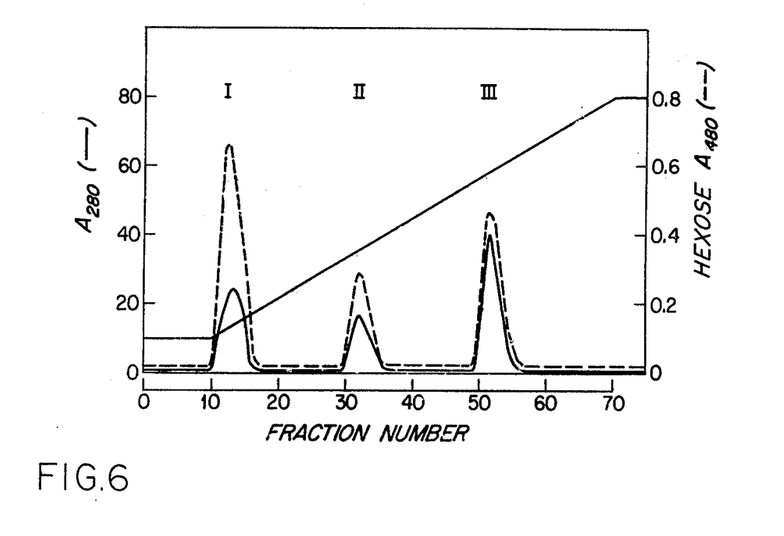

FIG. 6 shows DEAE-cellulose column chromatography of charcoal/Celite column eluate fraction of Cl which contained inhibitor activity. Charcoal/Celite column fraction Cl (Table 1) was concentrated under nitrogen and applied in a volume of 0.5 ml to a column (0.9 cm×60 cm) of DEAE-cellulose equilibrated in 0.0005 M-sodium phosphate buffer, pH 7.5. The column was developed with an increasing concentration gradient (. . . , 0.005-0.03 M) at a rate of 16 ml/h, 5 ml fractions were collected. Fractions were assayed for neutral hexose by the phenol/H$_2$SO$_4$ method (Dubois et al, Anal. Chem., 28, 350-357, 1956 and protein by continuous monitoring at 280 nm (———). Fractions were pooled as indicated and characterized for inhibition of UDP-galactose-SGF-fetuin acceptor galactosyltransferase activity (Table 2) and for the ability to act as a galactosyltransferase acceptor. (FIG. 4).

Figure 7:
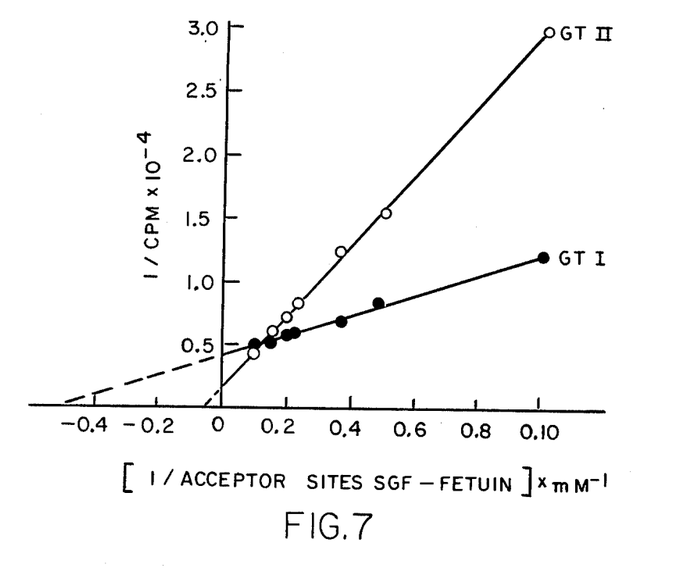

FIG. 7 shows the determination of $K_m$ for cancer-associated galactosyltransferase acceptor for galactosyltransferase activity by using purified normal isoenzyme GT-I (0) or purified cancer-associated isoenzyme GT-II. Isoenzymes GT-I and GT-II were purified from human malignant effusion. $K_m$ for cancer-associated galactosyltransferase acceptor was determined as described in FIG. 3, except that purified acceptor (peak I, FIG. 6) was substituted for SGF-fetuin, and incorporation was determined as described above and in FIG. 4. Data are plotted by the Lineweaver-Burk (1934) method, assuming a mol. wt. for cancer-associated galactosyltransferase acceptor of 3600. Calculated $K_m$ values are for isoenzyme GT-I, 500 μM; for isoenzyme GT-II, 20 μM.

TABLE I

CHARCOAL/CELITE CHROMATOGRAPHY OF SERUM FILTRATES IN SEPARATION OF AN INHIBITOR OF UDP-GALACTOSE-SGF-FETUIN ACCEPTOR GALACTOSYLTRANSFERASE ACTIVITY

Sera (1.0 ml) were heat-inactivated (60° C., 20 min) and the ultrafiltrate from an Amicon PM-10 membrane was obtained. The ultrafiltrate was placed on charcoal/Celite columns (1 mg/ml of hexose) and eluted in stepwise fashion with increasing concentrations of ethanol. Inhibition of activity was measured as described in the Experimental section, after adjustment of concentration to include 1 μg hexose per 10 μl sample.

| Serum | Fraction | Ethanol (%) | Inhibition (%) | Hexose (mg) | Protein (mg) |
|---|---|---|---|---|---|
| Cancer | C1 | 0 | 47 | 2.50 | 0.025 |
|  | C2 | 17 | — | 1.20 | 0.160 |
|  | C3 | 20 | — | <0.01 | 0.040 |
|  | C4 | 25 | — | <0.01 | 0.050 |
|  | C5 | 30 | — | <0.01 | 0.020 |
|  | C6 | 50 | 8 | 0.03 | 0.210 |
| Normal | N1 | 0 | 4 | 3.20 | 0.320 |
|  | N2 | 17 | — | 0.42 | 0.060 |
|  | N3 | 20 | — | 0.40 | 0.140 |
|  | N4 | 25 | — | <0.01 | 0.030 |
|  | N5 | 30 | — | <0.01 | 0.030 |
|  | N6 | 50 | 3 | <0.01 | 0.030 |

TABLE 3

INHIBITION OF UDP-GALACTOSE-SGF-FETUIN ACCEPTOR GALACTOSYL-TRANSFERASE BY THE THREE MAJOR PEAKS ELUTED FROM DEAE-CELLULOSE

Malignant effusion (10 ml) was heat-inactivated (60° C., 20 min) and the Amicon PM-10 membrane ultrafiltrate obtained. Charcoal/Celite chromatography was performed as described in Table 1. Fraction C1 was concentrated and applied to a column (0.9 cm × 50 cm) of DEAE-cellulose equilibrated in 0.0005 M-sodium phosphate buffer, pH 7.6. The column was developed with an ascending sodium phosphate buffer gradient as shown in FIG. 5. Peaks were pooled and assayed for hexose (Dubois et al, 1956) and protein (Lowry et al, J. Biol. Chem., 193, 1672–1676, 1951). Inhibition assay was performed by using a 10 μl sample adjusted to contain 1 μg of hexose. Inhibition assay was performed as described above.

| Peak | Hexose (mg) | Protein (mg) | Inhibition (%) |
|---|---|---|---|
| 1 | 0.43 | 0.08 | 86 |
| 2 | 0.05 | 0.02 | 6 |
| 3 | 0.26 | 0.10 | 3 |

TABLE 3

CARBOHYDRATE COMPOSITION OF CANCER ASSOCIATED GALACTOSYLTRANSFERASE ACCEPTOR

Hexose, hexosamine and sialic acid contents were determined by phenol/$H_2SO_4$ (Dubois et al, 1956), Elson-Morgan (Blix, Acta. Chem. Scand., 2, 467–473, 1948) and Warren J. Biol. Chem., 234, 1975, 1975 (1959) methods respectively after acid hydrolysis (6 M-HCl, 90° C., 120 min). G.l.C. evaluation of carbohydrate composition was carried out as described in the Experimental section, with inositol as an internal standard. Data are expressed as mol/mol of glycopeptide, based on a mol. wt. of 3600 determined by Bio-Gel P-10 polyacrylamide-gel.

| Method | Type | Carbohydrate Content (mol/mol of glycopeptide) |
|---|---|---|
| Assay | Neutral hexose | 3.9 |
| | Hexosamine | 8.7 |
| | Sialic acid | 0.3 |
| g.l.c. | Fucose | 0.0 |
| | Galactose | 0.1 |
| | N-Acetylglucosamine | 9.2 |
| | N-Acetylgalactosamine | 0.0 |
| | Mannose | 4.2 |

TABLE 4

AMINO ACID COMPOSITION OF CANCER ASSOCIATED GALACTOSYLTRANSFERASE ACCEPTOR

G.l.c. of amino acid derivatives was carried out as described above by using a Perkin-Elmer 900 g.l.c. instrument with attached chromatodigital integrator. Values are expressed as mol of residue/mol of glycopeptide based on a mol. wt. of 3600 determined by Bio-Gel P-10 polyacrylamide-gel chromatography.

| Amino Acid | Amount (mol/mol of glycopeptide) |
|---|---|
| Alanine | 1.2 |
| Valine | — |
| Glycine | 1.1 |
| Isoleucine | — |
| Leucine | 0.9 |
| Proline | — |
| Threonine | — |
| Serine | 0.7 |
| Phenylalanine | — |
| Asparagine/aspartic acid | 2.3 |
| Glutamine/glutamic acid | 2.7 |
| Lysine | 0.8 |
| Tyrosine | 1.1 |
| Hydroxylysine | — |

EXAMPLE II

This example illustrates that the product of this invention inhibits the growth of transformed cells and tumors and can destroy malignant cells and tumors.

ASSAY OF GALACTOSYLTRANSFERASE ACTIVITIES

UDP-[$^3$H]-galactose (2.25 Ci/mole) was obtained from New England Nuclear. A stock solution, 714 μM, was prepared to a final specific activity of 0.227 Ci/m-mole using unlabelled UDP-galactose obtained from Sigma Chemical Co. The exogenous acceptor, SGF-fetuin, was prepared as described by Kim et al, J. Biol. Chem., 246, 5466–5476.

Galactosyltransferase activity was measured by modification of the method described by Podolsky et al, Biochem. J., 146, 215–221, (1971). The assay mixture included 10 μl of UDP-$^3$H-galactose stock solution, 35 μl of 0.1 M sodium cacodylate, pH 7.4, in 0.154 M NaCl, 7.5 μl of 0.1 M $MnCl_2$ and 20 μl of the acceptor SGF-fetuin, which contained 0.2 μm acceptor sites. The mixture (75 μl) was incubated for 60 min at 37°. The reaction was terminated by addition of 5% phosphotungstic acid (w/v) in 2 M HCl, and incorporation of radioactive label into acid precipitable material was determined.

PREPARATION OF CAGA

Purified human cancer-associated galactosyltransferase acceptor (CAGA) was prepared from pooled malignant effusions by sequential chromatography on charcoal-celite and DEAE-cellulose columns as set forth in Example I. CAGA was shown to be homogeneous by three paper electrophoretic systems and one descending chromatographic system.

PREPARATION OF CELLS AND MEDIA

Baby hamster kidney cells (BHK), NIL, baby hamster kidney cells transformed with polyoma virus (BHKpygiv) and NIL cells transformed with polyoma virus (NILpy) cells were grown in Dulbecco's medium containing 10 percent fetal calf serum (heat-inactivated at 60°, 10 min). The BHKpygiv cells is a BHKpy mutant capable of growth in the absence of glutamine. All cells were examined for morphology, and harvested using 0.54 mM EDTA at varying times after plating for determination of cell number. Viability was determined by trypan blue exclusion. Media were also collected at this time for measurement of enzyme activity.

BT-20 cells derived from a primary human breast adenocarcinoma were grown as described by Las Fargues et al, J. Natl. Cancer Inst., 21, 1131–1145, except that the cells were maintained in media containing 15 percent heat-inactivated fetal calf serum (60°, 10 min). Human pancreatic carcinoma cells and Chang cells, derived from human liver, were grown under similar conditions.

PREPARATION OF TUMORS

Newly weaned hamsters (Charles River Laboratories) were inoculated with $1.0 \times 10^5$ BHKpy or BHKpygiv cells in 0.1 ml of NaCl/Pi by subcutaneous injection in the flank. Animals were sacrificed at different times and tumors were immediately excised and washed in cold 0.1 M sodium cacodylate, pH 7.4, in 0.154 M NaCl prior to weighing.

EFFECT OF CAGA ON GROWTH IN VITRO AND IN VIVO

Cells were maintained in culture as described above. Sterilized, purified CAGA in varying concentrations was added to the heat-inactivated fetal calf serum at the time of plating. Morphology and cell multiplication were determined at 24 and 48 hour intervals and compared to controls containing no addition or heat-inactivated whole serum from which CAGA had been removed by chromatography on charcoal-celite as described in Example I.

Effect of CAGA on tumor growth in vivo was determined by injection of CAGA (subcutaneously or intraperitoneally) into hamsters at the time of their inoculation with BHKpy cells or subsequent to the appearance of a palpable tumor. Animals were injected with 20 µg sterile CAGA in a volume of 0.1 ml NaCl/Pi per injection. Control animals were injected with either water, serum or heat-inactivated serum from which CAGA had been removed. Animals were sacrificed at various times (4–20 days) and tumors excised, washed in cold 0.154 M NaCl and weighed.

Figure 8:
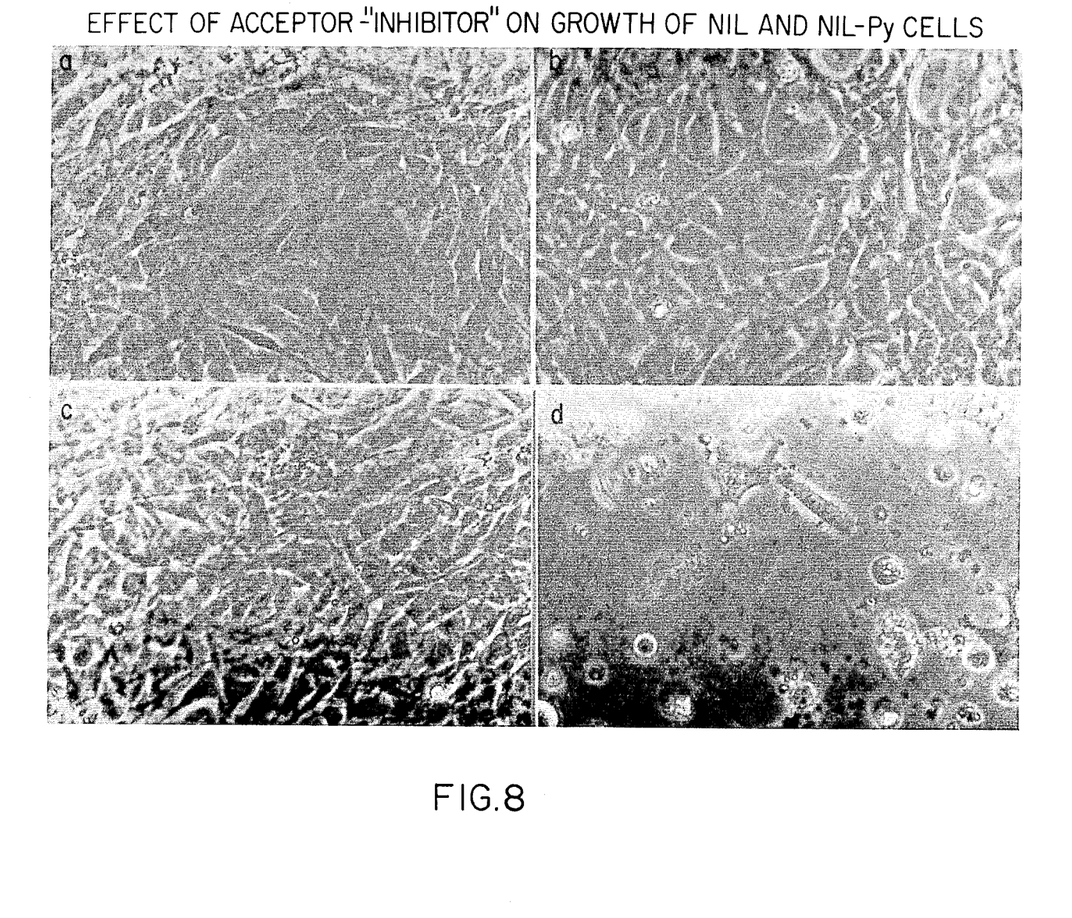

The effect of cancer-associated galactosyltransferase acceptor (CAGA), a glycopeptide, was assessed on the growth of tissue culture cells. The purified glycopeptide (3 µg) was added to the medium of both BHK and BHKpy cells at the time of seeding and cells were examined at 24 and 48 hr intervals. As shown in FIG. 8, addition of CAGA caused a marked change in the morphology of transformed cells but not in their nontransformed counterparts. Treated cells appeared more rounded and possessed both vacuolar and refractile inclusions. However, the effect on cell division was even more dramatic. Transformed cells grown in the presence of CAGA had one-tenth the number of cells compared to those grown in the absence of this glycopeptide (Table 8). Only minimal inhibition of growth was observed when CAGA was added to cultures of nontransformed BHK cells. No inhibition of growth or alteration of morphology was observed in either BHK or BHKpy control cultures to which CAGA-depleted effusion material or CAGA-depleted serum was added. (CAGA was removed by charcoal-celite chromatography). The same inhibition seen with human CAGA was observed when CAGA was purified from sera of hamsters bearing large tumors (data not shown). The effect of human CAGA on transformed cells was not reversed by continued culture in fresh media free of CAGA. As FIG. 9 reveals, there was a persistent suppression of transformed cell growth over a five-day period. Moreover, inhibition of growth of transformed cells was observed at concentrations as low as 1 µg CAGA/dish (0.3 nmole/2 ml). Similar suppression of growth and changes in morphology were observed for NILpy and BHKpygiv cells as well as for the BT-20 human mammary adenocarcinoma line and a human pancreatic carcinoma line. Growth of the non-transformed NIL line and the normal human liver Chang cell line was unaffected by addition of CAGA to media (Table 8).

Transformed cells also have been found to release large amounts of galactosyltransferase into the growth medium, Weiser et al, Prac. Natl. Acad. Soc., USA, 23, 1319-1322. Since this activity was found to correlate with growth, the media of CAGA-suppressed cells was examined for galactosyltransferase activity. The appearance of galactosyltransferase activity in the media of CAGA-suppressed cells was markedly diminished when compared to cultures not containing CAGA. The low levels of galactosyltransferase activity measured with SGF-fetuin acceptor were not due to the presence of the inhibitor, CAGA, since galactosyltransferase activity was not decreased in BHK cell cultures which contained CAGA.

The effect of CAGA on tumor growth in animals was also evaluated. In one series of experiments, hamsters were injected either subcutaneously or intraperitoneally with 20 µg of purified CAGA at the time of inoculation with tumorigenic BHKpygiv cells. As Table 9 shows, after 20 days the animals receiving CAGA had significantly smaller tumors (by weight). Inhibition of tumor growth was more marked after local, subcutaneous injection (70 percent decrease) than after systemic, intraperitoneal administration (40 percent decrease).

In other experiments, animals were injected subcutaneously with CAGA near the site of tumor inoculation or systemically at different times after inoculation. One group received CAGA at the time of inoculation; another group received CAGA twelve days later, at the first appearance of palpable tumor nodules. Again, both local and systemic CAGA inhibited tumor growth when CAGA was given at the time of inoculation, although the local route appeared somewhat more effective (Table 10, FIG. 10). However, animals given CAGA only after the appearance of tumor (Group IV, V) still demonstrated a significant reduction in tumor size, as measured ten days later (Table 10, FIG. 10). Subcutaneous injection near the site of tumor inoculation was still more effective than intraperitoneal injection, although both caused significant reduction in tumor size and weight.

The effect of repeated administration of CAGA on growth of established tumors was investigated. Hamsters were injected with a single (20 µg) or double 40 µg) dose of CAGA subcutaneously or intraperitoneally after the appearance of palpable tumor. Animals received seven more injections on alternate days until they were sacrificed and the effect on tumor weight determined. As shown in Table 11, marked reduction in tumor weight was observed in all groups, but those animals receiving 40 µg doses had smaller tumors than those receiving 20 µg doses. Most notable was the finding that several animals no longer had evidence of tumor at the time of sacrifice, although all animals were known to have palpable tumors prior to the first injection of CAGA.

Figure 9:
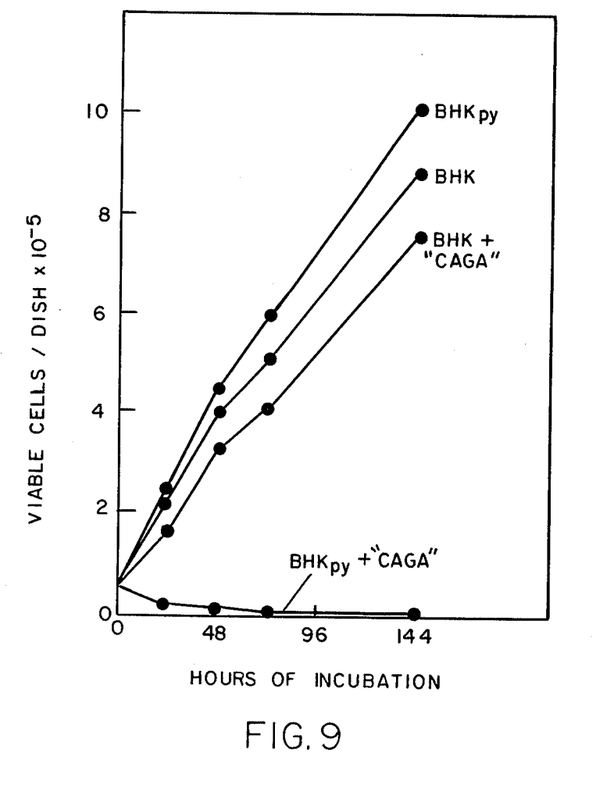

FIGS. 8 and 9 and Table 8 show that CAGA caused a selective growth suppression of transformed cells in tissue culture. Those transformed cells that survived exhibited a markedly altered morphology. At CAGA concentrations of 100 µg/dish (2 ml), a modest alteration in nontransformed cell morphology occurred although growth curves were not significantly different from those of control cultures. However, at lower doses of 1–10 µg/dish, only the growth of transformed cells was affected. These findings show that the effect of CAGA is dose-related and the suppression of growth is related to an increased sensitivity of transformed or tumor cells to CAGA.

Experimentation with other cell types (Table 8) revealed that the selective inhibition of transformed cell growth was not limited to the BHK and BHKpy paired cell lines. Inhibition of growth of NILpy cells was also seen, while NIL cell growth was unaffected. Human tumor cell lines were also inhibited; this was in contrast to Chang cells, a normal human liver derived cell line, which grew without difficulty. These findings show that the effect of CAGA is not species specific and that its special effect on transformed cells appears to be consistent.

Figure 10:
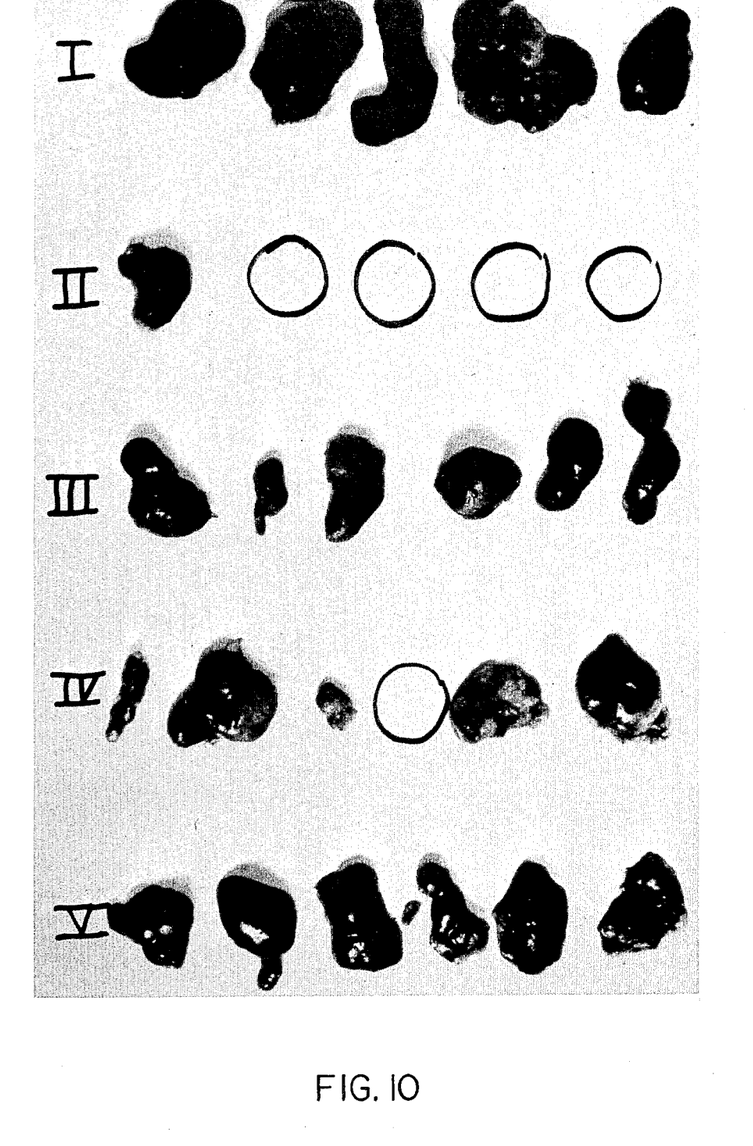

As shown in Table 9, both local and systemic administration of CAGA retarded tumor growth when the glycopeptide was given at the time of inoculation of the tumorigenic cells. The enhanced effect of locally administered CAGA may be related to its direct (local) toxic effect on the BHKpy cells. However, inhibition of tumor growth was also observed when a similar dose of CAGA was given systemically at a site distant from the nascent tumor. It is noteworthy that the effect on tumor growth could be observed even after a significant tumor had formed (Tables 10 and 11). Indeed, in some animals, established tumors diminished in size after repeated CAGA administration (FIG. 10).

In one experiment, a group of six hamsters died within 24 hr of administering an initial dose of CAGA. It is likely that this event was due to contamination of the preparation since no further problems have been encountered subsequently with other CAGA preparations. Although the potential toxicity of CAGA has not been fully evaluated, not other adverse effects have been observed after its administration. Control (non-tumor bearing) animals injected with CAGA could not be distinguished from noninjected controls after two weeks of observation.

These data show that the glycopeptide CAGA inhibits growth of tumor in vitro and in vivo but the mechanism of this inhibition remains to be determined. The ability of CAGA to inhibit the growth of transformed cells in vitro clearly shows that CAGA can exert its effect in the absence of any component of the primary mechanism in the intact animal. It is also posible that the inhibition of tumor cell growth by CAGA is related to its ability to act as a substrate for tumor galactosyltransferase. Indeed, CAGA-induced growth suppression was correlated with suppression of galactosyltransferase shedding by transformed cells, although this may be an effect rather than a cause of cell-growth inhibition.

FIG. 8 shows cells grown with or without purified human CAGA in presence of 5% heat-inactivated fetal calf serum.

(a) Nil cells, (b) Nil cell+3 $\mu$g CAGA, (c) Nilpy cells, (d) Nilpy cell+3 $\mu$g CAGA. All at 24 hrs. after seeding.

FIG. 9 shows the effect of CAGA on cell growth in vitro. BHK and BHKpy cells were seeded ($10^5$/dish) and grown in 10% heat-inactivated fetal calf serum, with or without human CAGA (3 $\mu$g/dish). Cells were harvested and counted as described at 24 hr intervals.

FIG. 10 shows the effect of CAGA on growh of tumors. Hamsters were inoculated with BHKpy cells as described above. Subsequently, animals were injected with 20 g CAGA either subcutaneously (S.C.) or intraperitoneally (I.P.) on the day of inoculation (day 1) or after the development of palpable tumors (day 15). Animals were sacrificed on day 21 and tumors excised. Group I=control; Group II—S.C. day 1; Group III-=I.P. day 1; Group IV=S.C., day 15; Group V=I.P., day 15. Open circles indicate animals without apparent tumor. Weights of tumors are compared in Table 11.

TABLE 8

EFFECT OF CAGA ON IN VITRO GROWTH OF NONTRANSFORMED, TRANSFORMED AND MALIGNANT CELLS

| Cell | Additions | |
|---|---|---|
| | Control | CAGA |
| | Cell Number | |
| BHK | $1.4 \times 10^6$ | $1.8 \times 10^6$ |
| NIL | $5.5 \times 10^5$ | $4.8 \times 10^5$ |
| Chang | $5.5 \times 10^5$ | $4.6 \times 10^5$ |
| BHKpy | $16.0 \times 10^5$ | $0.8 \times 10^5$ |
| BHKpygiv | $3.6 \times 10^6$ | $0.6 \times 10^6$ |
| NILpy | $1.0 \times 10^6$ | $0.1 \times 10^6$ |
| Human mammary carcinoma (BT-20) | $8.0 \times 10^5$ | $0.4 \times 10^5$ |
| Human Pancreatic carcinoma | $2.2 \times 10^5$ | $0.8 \times 10^5$ |

Cells were seeded ($1 \times 10^5$ cells/dish) and grown in 10% heat-inactivated fetal calf serum as described above. Medium was supplemented with either buffer or purified CAGA (5 $\mu$g) from human malignant effusion. Cells were harvested after 96 hrs incubation. NIL and NILpygiv cells are pictured in FIG. 9.

TABLE 9

EFFECT OF CAGA ON INITIATION OF TUMOR GROWTH

| Group | Material Injected | Site | Tumor Weight | Mean Inhibition (of tumor growth/size |
|---|---|---|---|---|
| | | | g | % |
| 1 | Buffer | Subcutaneous | 22.2 ± 3.8 | 0 |
| 2 | CAGA | Subcutaneous | 6.9 ± 2.1 | 69 |
| 3 | CAGA | Intraperitoneal | 13.5 ± 4.0 | 39 |

Weanling outbred hamsters (6 per group) were inoculated subcutaneously with $1 \times 10^5$ BHKpygiv cells. Subsequently, animals were injected with either buffer or purified human CAGA (20 $\mu$g) in a volume of 100 $\mu$l. Animals were sacrificed 22 days after inoculation. Tumors were dissected free, washed and weighed. Weights expressed as mean±SE. In addition, animals injected with CAGA-depleted effusion failed to show any reduction in tumor weight in subsequent experiments.

TABLE 10

EFFECT OF CAGA ON GROWTH OF ESTABLISHED TUMOR IN HAMSTERS

| Group | CAGA Injection | | Tumor Weight | Mean Inhibition (of tumor weight) |
|---|---|---|---|---|
| | Site | Day of Injection | | |
| | | | g | % |
| 1 | Control | — | 6.5 1.1 | 0 |
| 2 | Subcutaneous | 1 | 0.4 0.3 | 94 |
| 3 | Intraperitoneal | 1 | 2.2 0.6 | 67 |
| 4 | Subcutaneous | 15 | 1.7 0.5 | 74 |
| 5 | Intraperitoneal | 15 | 2.7 0.5 | 59 |

Hamsters were inoculated with BHKpy cells ($1 \times 10^5$/animal) and subsequently injected with buffer or CAGA (20 $\mu$g/100 $\mu$l) on day of inoculation or after development of palpable tumor (approximately 0.5 cm) on day 15 after inoculation. Animals were sacrificed on day 21 and tumors were dissected, washed and weighed. Weights expressed as mean±SD. Each group consisted of 6 animals.

TABLE 11
EFFECT OF REPEATED CAGA ADMINISTRATION OF GROWTH OF ESTABLISHED TUMORS IN HAMSTERS

| Group | CAGA Injection Site | Amount (μg) | Tumor Weight (g) | Inhibition (of tumor wt) (%) |
|---|---|---|---|---|
| 1 | Control | 0 | 16.1 ± 4.2 | 0 |
| 2 | Subcutaneous | 20 | 7.4 ± 2.3 | 54 |
| 3 | Intraperitoneal | 20 | 11.2 ± 3.6 | 30 |
| 4 | Subcutaneous | 40 | 6.1 ± 1.8 | 62 |
| 5 | Intraperitoneal | 40 | 2.4 ± 1.5 | 85 |

Hamsters were inoculated with BHKpygiv cells ($1 \times 10^5$/animal). Palpable tumors were evident by day 12-14 (approximately 0.5 cm). Animals were injected with buffer or human CAGA on day 15. Injections were repeated on alternate days until sacrifice on day 30. Tumors were dissected, washed and weighed and data expressed as mean±SD. Each group represented 6 animals.

What we claim is:

1. A composition of matter derived from the body fluids of animals having cancer or from extracts of malignant cells or tumor and being capable of inhibiting the growth of malignant cells or tumors comprising:
a glycoprotein having a molecular weight of about 3600, said glycoprotein comprising a substrate for the GT-I and GT-II isoenzymes of serum glactosyltransferase and having a molecular weight of 3600 and having an affinity for said GT-I isoenzyme of about 500 μM and for said GT-II enzyme of about 20 μM, said affinity being based upon a molecular weight of 3600 for said glycoprotein, said glycoprotein having the property of inhibiting the growth of malignant cells and malignant tumors,
said composition of matter being obtained by isolating a body fluid or an extract of malignant cells or a malignant tumor containing a glycoprotein having a molecular weight of about 3600 and comprising a substrate for the GT-I and GT-II isoenzymes of serum glactosyltransferase, passing said body fluid or extract serially through two separation columns, one of said columns containing a material which concentrates glycoprotein in said body fluid or extract and the other of said columns containing a material which concentrates components in said body fluid or extract having a molecular weight of about 3600.

2. The composition of claim 1 which contains components of the body fluid or cell extract having a molecular weight of about 3600 which components do not inhibit the capability of the glycoprotein to inhibit the growth of malignant cells or malignant tumors.

3. The process of isolating a glycoprotein composition having the property of inhibiting the growth of malignant cells or tumors which comprises isolating a body fluid or an extract of malignant cells or a malignant tumor containing a glycoprotein having a molecular weight of about 3600 and comprising a substrate for the GT-I and GT-II isoenzymes of serum glactosyltransferase, passing said body fluid or extract serially through two separation columns, one of said columns containing a material which concentrates glycoproteins in said body fluid or extract and the other of said columns containing a material which concentrates components in said body fluid or extract having a molecular weight of about 3600.

4. The process of claim 3 wherein said body fluid or extract is passed first through the column containing the material which concentrates glycoprotein.

5. The process of claim 3 wherein said body fluid or extract is subjected to an initial separation step to separate components in the body fluid or extract having a molecular weight above about 5000 from components in the body fluid or extract having a molecular weight below about 5000 and passing the components having a molecular weight below about 5000 through said columns.

6. The process of claim 1 wherein the liquid obtained from the first separation column is partially evaporated under vacuum prior to being introduced into the second separation column.

7. The process for inhibiting the growth of malignant cells or tumors in an animal which comprises administering the composition of claim 1 to said animal.

8. The process for inhibiting growth of malignant cells or tumors in an animal which comprises administering the composition of claim 2 to said animal.

* * * * *